(12) United States Patent
Bray et al.

(10) Patent No.: US 11,766,437 B2
(45) Date of Patent: Sep. 26, 2023

(54) COMBINATION THERAPIES FOR INHIBITION OF TTK PROTEIN KINASE

(71) Applicant: UNIVERSITY HEALTH NETWORK, Toronto (CA)

(72) Inventors: Mark Robert Bray, Oakville (CA); Jacqueline M. Mason, Toronto (CA); Tak W. Mak, Toronto (CA); Graham Fletcher, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 390 days.

(21) Appl. No.: 16/635,320

(22) PCT Filed: Aug. 1, 2018

(86) PCT No.: PCT/CA2018/050936
§ 371 (c)(1),
(2) Date: Jan. 30, 2020

(87) PCT Pub. No.: WO2019/023799
PCT Pub. Date: Feb. 7, 2019

(65) Prior Publication Data
US 2020/0230144 A1   Jul. 23, 2020

(30) Foreign Application Priority Data

Aug. 1, 2018  (WO) ................ PCT/CA2017/050920

(51) Int. Cl.
*A61K 31/519* (2006.01)
*A61P 35/00* (2006.01)
*A61K 39/395* (2006.01)

(52) U.S. Cl.
CPC ........ *A61K 31/519* (2013.01); *A61K 39/3955* (2013.01); *A61P 35/00* (2018.01)

(58) Field of Classification Search
None
See application file for complete search history.

(56) References Cited

FOREIGN PATENT DOCUMENTS

| CA | 2949121 A1 | 11/2015 |
|----|------------|---------|
| CA | 2954508 A1 | 1/2016 |

(Continued)

OTHER PUBLICATIONS

Kwok et al. Pembrolizumab (Keytruda). Human Vaccines & Immunotherapeutics (2016) 12(11) 2777-2789 (Year: 2016).*

(Continued)

*Primary Examiner* — Joanne Hama
*Assistant Examiner* — Miles Joseph Delahoussaye
(74) *Attorney, Agent, or Firm* — McCarter & English, LLP; Steven G. Davis; Wei Song (57) ABSTRACT

Provided herein are methods of treating cancer using an effective amount of a compound represented by the formula: (I) or a pharmaceutically acceptable salt thereof and an effective amount of an immune checkpoint inhibitor. Also provided are compositions comprising the same compound represented by the formula shown above or a pharmaceutically acceptable salt thereof and an immune checkpoint inhibitor.

(Continued)

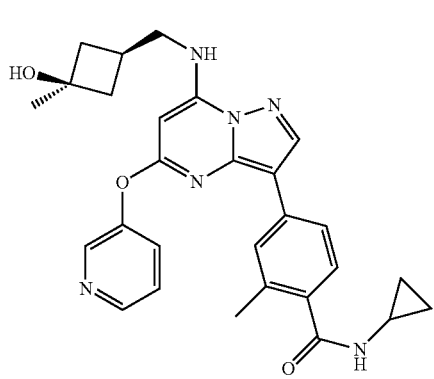

(I)

13 Claims, 4 Drawing Sheets

(56) References Cited

FOREIGN PATENT DOCUMENTS

| CA | 2963281 A1 | 4/2016 | |
|---|---|---|---|
| CA | 2966042 A1 | 5/2016 | |
| WO | WO-2015070349 A1 * | 5/2015 | ........... A61K 31/519 |

OTHER PUBLICATIONS

Mason et al. Functional characterization of CFI-402257, a potent and selective Mps1/TTK kinase inhibitor, for the treatment of cancer. PNAS(2017) 114(12) 3127-3132 (Year: 2017).*

Bio X Cell store page for RMP1-14 Cat. # BE0146. https://bxcell.com/product/invivomab-anti-m-pd-1/ accessed May 5, 2022 (Year: 2022).*

Maia et al (inhibition of the spindle assembly checkpoint kinase TTK enhances the efficacy of docetaxel in a triple-negative breast cancer model. Annals of Oncology (2015) 26(10):2181-2192 and supplemental data (Year: 2015).*

Liu et al., Discovery of Pyrazolo[1,5-a]pyrimidine TTK Inhibitors: CFI-402257 is a Potent, Selective, Bioavailable Anticancer Agent. ACS Med Chem Lett. May 6, 2016;7(7):671-5.

Mason et al., Functional characterization of CFI-402257, a potent and selective Mps1/TTK kinase inhibitor, for the treatment of cancer. Proc Natl Acad Sci U S A. Mar. 21, 2017;114(12):3127-3132.

International Search Report and Written Opinion for Application No. PCT/CA2017/050920, dated Apr. 17, 2018, 13 pages.

International Search Report and Written Opinion for Application No. PCT/CA2018/050936, dated Oct. 30, 2018, 13 pages.

* cited by examiner

COMBINATION THERAPIES FOR INHIBITION OF TTK PROTEIN KINASE

CROSS REFERENCE TO RELATED APPLICATIONS

This reference is a U.S. national stage application filed under 35 U.S.C. § 371(c), of International Application No. PCT/CA2018/050936, filed on Aug. 1, 2018, which claims priority to International Patent Application No. PCT/CA2017/050920, filed on Aug. 1, 2017. The entire teachings of each of the aforementioned applications are incorporated herein by reference.

BACKGROUND

CFI-402257 is a compound represented by the formula:

that inhibits TTK protein kinase (also known as Monopolar spindle 1 or Mps1) activity. TTK is a core protein of the spindle assembly checkpoint (SAC), which is a signaling cascade that prevents chromosome missegregation by arresting the cell cycle in mitosis until all chromosomes are properly attached to the mitotic spindle. Thus, the SAC ensures healthy proliferation and precise division in cells. Many cancer cells have a weakened SAC response that may contribute to malignancy. However, more severe disabling of the SAC generates a level of chromosome instability that exceeds the adaption capacity of cancer cells, and is a potential anticancer strategy. Many tumors are shown to over-express TTK, which correlates with worse prognosis. Inhibition of TTK activity in cancer cells causes severe chromosome missegregation, cell death and inhibited tumor growth.

CFI-402257 is presently undergoing a phase I clinical trial (ClinicalTrials.gov ID NCT02792465) with patients having advanced solid cancers. Given the potency and selectivity of CFI-402257 in inhibiting a critical mitotic checkpoint protein, it would be advantageous to further enhance the efficacy of this drug candidate in cancer treatment.

SUMMARY

It has now been found by the inventors of the present application that the administration of the compound CFI-402257 or a pharmaceutically acceptable salt thereof and an immune checkpoint inhibitor synergistically treats cancer. See e.g., FIGS. 1D and 2D, which both illustrate complete tumor regression in the syngeneic CT26 mouse colon carcinoma model upon administration of a combination of the compound CFI-402257 or a pharmaceutically acceptable salt thereof and the rat IgG2a anti-PD-1 antibody. Importantly, when the animals in which complete regression have occurred are re-challenged by inoculation with the same cancer cells, tumors did not grow in any of these animals, thereby indicating that immunity to the cancer cells has been generated by the CFI-402257-anti-PD-1-antibody combination therapy. Furthermore, animals that are subjected to this combination therapy do not suffer from any significant body weight loss, thereby indicating that both agents at at least the administered dosages are well-tolerated.

Based on these results, provided herein are methods of treating cancer in a subject, by administering to the subject an effective amount of the compound CFI-402257 or a pharmaceutically acceptable salt thereof and an effective amount of an immune checkpoint inhibitor as described herein.

Also provided herein are pharmaceutical compositions comprising the compound CFI-402257 or a pharmaceutically acceptable thereof and an immune checkpoint inhibitor as described herein.

DETAILED DESCRIPTION

In one aspect, the present disclosure provides a method of treating cancer in a subject, comprising the step of administering to the subject an effective amount of the compound CFI-402257 that is represented by the formula:

or a pharmaceutically acceptable salt thereof and an effective amount of an immune checkpoint inhibitor.

It will be understood that unless otherwise indicated, the administrations described herein include administering the described compound CFI-402257 or a pharmaceutically acceptable salt thereof prior to, concurrently with, or after administration of the immune checkpoint inhibitor described herein. Thus, simultaneous administration is not necessary for therapeutic purposes. In one embodiment, however, the compound CFI-402257 or a pharmaceutically acceptable salt thereof is administered concurrently with the immune checkpoint inhibitor.

The compound CFI-402257 described herein has basic amine groups and therefore can form pharmaceutically acceptable salts with pharmaceutically acceptable acid(s). Accordingly, the term "pharmaceutically acceptable salt" as used herein refers to any suitable pharmaceutically acceptable acid addition salt of the compound CFI-402257 described herein, which includes but is not limited to salts of inorganic acids (e.g., hydrochloric acid, hydrobromic, phosphoric, nitric, and sulfuric acids) and of organic acids (such as, acetic acid, benzenesulfonic, benzoic, methanesulfonic, and p-toluenesulfonic acids). Other examples of such salts include hydrochlorides, hydrobromides, sulfates, methanesulfonates, nitrates, benzoates, fumarates, maleates, bisphosphate hemihydrates and salts with amino acids such as glutamic acid.

As used herein, an "immune check point inhibitor" or simply a "checkpoint inhibitor" refers to any compound that, either directly or indirectly, decreases the level of or inhibits the function of an immune checkpoint receptor protein found on the surface of an immune cell (e.g., T-cells, B-cells, etc.). Alternatively, the immune checkpoint inhibitor is a compound that, either directly or indirectly, decreases the level of or inhibits the function of a ligand on the surface of an immune cell-inhibitory cell (e.g., regulatory T-cells, tolerogenic antigen presenting cells (APC), myeloid-derived suppressor cells (MDSC), tumor-associated macrophages (TAM), cancer-associated fibroblasts (CAF), other cancer cells and APCs, etc.), or secreted by an immune cell-inhibitory cell. This ligand is typically capable of binding the immune checkpoint receptor protein of the immune cell. A non-limiting example of an immune checkpoint receptor protein-ligand pair is PD-1/PD-L1. PD-1 is an immune checkpoint receptor protein found on T-cells. PD-L1 that is often over-expressed by cancer cells binds to PD-1 and helps the cancer cells evade the host immune system attack. Accordingly, an immune checkpoint inhibitor prevents or reverses this PD-1/PD-L1 binding, by either blocking the PD-1 on the T-cells (i.e., a PD-1 inhibitor) or the PD-L1 on the cancer cells (i.e., a PD-L1 inhibitor), thereby maintaining or restoring anti-tumor T-cell activity or blocking T-cell-inhibitory cell activity. Additionally, an immune checkpoint inhibitor refers to a compound as described in US Patent Application Publication Nos. US 2017/0190675 and US 2016/0185870, and International Patent Application Publication Nos. WO 2015/112900, WO 2010/027828 and WO 2010/036959.

An immune checkpoint inhibitor in accordance with the present invention may be a small-molecule organic compound or a large molecule such as a peptide or a nucleic acid. In at least one embodiment, an immune checkpoint inhibitor is an antibody or an antigen binding fragment thereof. In at least one embodiment, an immune checkpoint inhibitor is a monoclonal antibody or an antigen binding fragment thereof.

As used herein, the term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (e.g., Fab, Fab', F(ab')$_2$, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc In some embodiments, an antibody is a non-naturally occurring antibody. In some embodiments, an antibody is purified from natural components. In some embodiments, an antibody is recombinantly produced. In some embodiments, an antibody is produced by a hybridoma.

The term "antibody fragment" refers to a portion of an intact antibody and refers to the antigenic determining variable regions of an intact antibody. Examples of antibody fragments include, but are not limited to, Fab, Fab', F(ab')$_2$, and F$_v$ fragments, linear antibodies, single chain antibodies, and multispecific antibodies formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) an Fab fragment, a monovalent fragment consisting of the V$_L$, V$_H$, C$_L$, and C$_H$ domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a $F_d$ fragment consisting of the $V_H$ and $C_{H1}$ domains (i.e., that portion of the heavy chain which is included in the Fab); (iv) a $F_v$ fragment consisting of the $V_L$ and $V_H$ domains of a single arm of an antibody, and the related disulfide linked $F_v$; (v) a dAb (domain antibody) or sdAb (single domain antibody) fragment (Ward et al., Nature 341:544-546, 1989), which consists of a $V_H$ domain; and (vi) an isolated complementarity determining region (CDR).

As used herein, a "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, F$_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., Nature 321:522-525, 1986; Riechmann et al., Nature 332:323-327, 1988; Verhoeyen et al., Science 239:1534-1536, 1988).

A non-exhaustive list of examples of an immune checkpoint inhibitor is provided as following: a CD40L inhibitor, a DR3 inhibitor, a TL1A inhibitor, a GITR inhibitor, a GITRL inhibitor, a 4-1BB inhibitor, a 4-1BBL inhibitor, an OX40 inhibitor, an OX40L inhibitor, a CD27 inhibitor, a CD70 inhibitor, a TMIGD2 inhibitor, an HHLA2 inhibitor, an ICOS inhibitor, an ICOSL inhibitor, a B7RP1 inhibitor, a CD28 inhibitor, a PD-1 inhibitor, a PD-L1 inhibitor, a PD-L2 inhibitor, a CTLA-4 inhibitor, a CD80 inhibitor, a CD86 inhibitor, a MR inhibitor, a TCR inhibitor, a LAG3 inhibitor, an MHCI inhibitor, an MHCII inhibitor, a CD80 inhibitor, a TIM-3 inhibitor, a GALS inhibitor, a BTLA inhibitor, an HVEM inhibitor, a CD160 inhibitor, a CD137 inhibitor, a CD137L inhibitor, a LIGHT inhibitor, a phosphatidylserine inhibitor, a VISTA inhibitor, a BTNL2 inhibitor, a B7-H3 inhibitor and a B7-H4 inhibitor. In certain embodiments, the immune checkpoint inhibitor applied in a cancer treatment method of the invention is one or more selected from the aforementioned examples.

In one embodiment, the immune checkpoint inhibitor is one or more selected from a PD-1 inhibitor, a PD-L1 inhibitor and a CTLA-4 inhibitor.

In one embodiment, the immune checkpoint inhibitor is a PD-1 inhibitor. In another embodiment, the immune checkpoint inhibitor is a PD-L1 inhibitor.

In some embodiments, the immune checkpoint inhibitor is one or more selected from pembrolizumab, ipilimumab, nivolumab, atezolizumab, avelumab and durvalumab.

In some embodiments, the immune checkpoint inhibitor is one or more selected from JS001, SHR-1210, BGB-A317, IBI-308, REGN2810, JS003, SHR-1316, KN035, BMS-936559, LAG525, BMS-986016, MBG453, MEDI-570, OREG-103/BY40 and lirilumab. In one embodiment, the immune checkpoint inhibitor is one or more selected fromCJS001, SHR-1210, BGB-A317, IBI-308 and REGN2810. In an alternative embodiment, the immune checkpoint inhibitor is one or more selected from JS003, SHR-1316, KNO35 and BMS-936559.

As used herein, the terms "treatment," "treat," and "treating" refer to reversing, alleviating, ameliorating, inhibiting or slowing the progression of a cancer, reducing the likelihood of recurrence of a cancer, or one or more symptoms thereof, as described herein. Exemplary types of cancer treated by the methods and compositions of the invention include but are not limited to breast cancer (including metastatic breast cancer); colon cancer; rectal cancer; colorectal cancer; lung cancer (including small-cell lung cancer (SCLC), non-small cell lung cancer (NSCLC), adenocarcinoma of the lung, and squamous carcinoma of the lung); cancer of the peritoneum; gastric or stomach cancer; gastrointestinal cancer; cervical cancer; liver cancer; bladder cancer; hepatoma; ovarian cancer; endometrial or uterine cancer; prostate cancer; testicular cancer; leukemias; lymphomas; hematological malignancies; brain cancer (including glioma, glioblastoma multiforme, medulloblastoma, and neuroblastoma); head and neck cancer; pancreatic cancer; melanoma; hepatocellular cancer; kidney or renal cancer; vulval cancer; thyroid cancer; hepatic carcinoma; anal carcinoma; penile carcinoma; Merkel cell cancer; mycoses fungoids; esophageal cancer; tumors of the biliary tract; salivary gland cancer; sarcomas; retinoblastoma; liposarcoma, synovial cell sarcoma; neuroendocrine tumors; gastrinoma; islet cell cancer; mesothelioma; schwannoma; acoustic neuroma; meningioma; adenocarcinoma; squamous cell cancer and epithelial squamous cell cancer. In another embodiment, the cancer treated by the methods and compositions of the invention is pancreatic cancer, lung cancer, breast cancer, colon cancer, brain cancer, neuroblastoma, prostate cancer, melanoma, glioblastoma multiforme, ovarian cancer, lymphoma, leukemia, melanoma, sarcoma, paraneospasia, osteosarcoma, germinoma, glioma or mesothelioma. In yet another embodiment, the cancer is renal cell carcinoma, non-small cell lung cancer, urothelial cancer, head and neck cancer, ovarian cancer, lymphoma, melanoma, pancreatic cancer, myeloma, acute myeloid leukemia, bladder cancer and Hodgkin's lymphoma.

The term "an effective amount" means an amount when administered to a subject which results in beneficial or desired results, including clinical results, i.e., reversing, alleviating, inhibiting or slowing the progression of a cancer, reducing the likelihood of recurrence of a cancer, or one or more symptoms thereof, e.g., as determined by clinical symptoms, the amount or volume or cancer cells or tumors in a subject compared to a control.

In an embodiment, an effective amount of the compound CFI-402257 or a pharmaceutically acceptable salt thereof taught herein ranges from about 0.1 to about 1000 mg/kg body weight, alternatively about 1 to about 500 mg/kg body weight, and in another alternative, from about 1 to about 100 mg/kg body weight, and in yet another alternative, from about 1 to about 50 mg/kg. In an embodiment, an effective amount of an immune checkpoint inhibitor taught herein ranges from about 0.01 to about 1000 µg per subject, alternatively from about 0.05 to about 500 µg per subject. The skilled artisan will appreciate that certain factors may influence the dosage required to effectively treat a subject suffering from cancer or reduce the likelihood of recurrence of a cancer. These factors include, but are not limited to, the classification and/or severity of the disease or disorder, previous treatments, the general health and/or age of the subject and other diseases present.

In another aspect, pharmaceutical compositions comprising the compound CFI-402257 or a pharmaceutically acceptable salt thereof and an immune checkpoint inhibitor are also included in the present disclosure.

Also included are the use of the compound CFI-402257 or a pharmaceutically acceptable salt thereof in the manufacture of a medicament to be used in combination with an immune checkpoint inhibitor as described herein for the treatment of one or more cancers described herein. Also included herein are pharmaceutical compositions comprising the compound CFI-402257 or a pharmaceutically acceptable salt thereof and an immune checkpoint inhibitor as described herein optionally together with a pharmaceutically acceptable carrier, in the manufacture of a medicament for the treatment of one or more cancers described herein. Also included is the compound CFI-402257 for use in combination with an immune checkpoint inhibitor as described herein for the treatment of a subject with cancer. Further included are pharmaceutical compositions comprising the compound CFI-402257 or a pharmaceutically acceptable salt thereof and an immune checkpoint inhibitor as described herein, optionally together with a pharmaceutically acceptable carrier, for use in the treatment of one or more cancers described herein. Further included are pharmaceutical compositions comprising the compound CFI-402257 or a pharmaceutically acceptable salt thereof and an immune checkpoint inhibitor as described herein optionally together with a pharmaceutically acceptable carrier for use in the treatment of one or more cancers described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

The compound CFI-402257 or a pharmaceutically acceptable salt thereof and the immune checkpoint inhibitor, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

EXEMPLIFICATION

While have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Example 1

Materials

Salt forms of the compound CFI-402257 were prepared using the one or more of the procedures described in U.S. Pat. No. 9,657,025, International Publication Application Nos. WO 2014/075168 and WO 2015/070349, and Liu et al. (2016) *ACS Med Chem Lett* 7(7):671-675. The hydrochloride or bisphosphate hemihydrate salt forms of the compound CFI-402257 were used in all of the studies described herein.

Rat IgG2a anti-PD-1 antibody (clone RMP1-14; cat. no. BE0146) and rat IgG2a isotype control (clone 2A3; cat. no. BE0089) were obtained from Bio X Cell.

BALB/cJ mice were obtained from The Jackson Laboratory. Six- to eight-week-old female animals were used for all of the studies described herein and were allowed unrestricted access to food and water. All animal procedures were approved by the institutional animal care and use committee of the University Health Network (Toronto).

The CT26 mouse colon carcinoma cell line was obtained from American Type Culture Collection (ATCC) and maintained according to the supplier's instructions. Short tandem repeat (STR) profiling was used to verify authenticity of the cell lines. Sixteen STR loci were simultaneously amplified in multiplex PCR at The Centre for Applied Genomics (Toronto), and the ATCC database was used for comparison when possible Cell lines were routinely tested for mycoplasma and used at low passage numbers (<15).

Example 2

Methods

BALB/cJ mice were inoculated subcutaneously with 1×10⁶ CT26 cells. The mice were then randomized. Animal weights were monitored daily, and tumor volume was measured three times per week.

Tumor volume (in cubic millimeters or mm³) was defined as $100\times[1-TV_{f, treated}-TV_{i, treated})/(TV_{f, control}-TV_{i, control})]$, where $TV_f$ is the average tumor volume at the end of study and $TV_i$ is the average tumor volume at the end initiation of treatment. In cases in which tumor regression occurred, percentage of tumor regression was defined as $100\times[1-(TV_{f, treated}/TV_{i, treated})]$. At the completion of each study, the mice were killed by an anesthetic overdose, and tumor tissue was removed for further analysis.

Treatments were initiated when tumor volumes reached an average size of ~60 mm³. To treat an established tumor, the animals were first assigned into groups, i.e., the control group receiving rat IgG2a PD-1 antibody, the group receiving the compound CFI-402257 monotherapy, the group receiving the rat IgG2a anti-PD-1 antibody monotherapy and the group receiving the combination therapy. The compound CFI-402257 and the vehicle [10% (v/v) NMP/40% (v/v) PEG-300/50% (v/v) water for the hydrochloride form; or 80-90% (v/v) PEG-300 or PEG-400 20-10% (v/v) water for the bisphosphate hemihydrate form] were administered by oral gavage (PO), at 6 mg/kg daily (QD) for 21 days. The anti-PD-1 antibody or the isotype control were administered by intraperitoneal (IP) injection. 150 μg anti-PD-1 antibody was administered in four doses, i.e., on Days 0, 3, 6 and 10. These treatment studies were carried out in duplicates.

Example 3

Figure 1A:
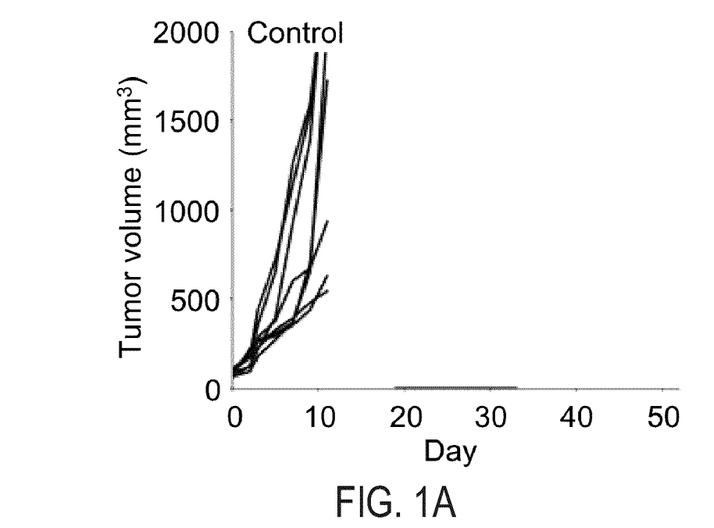
FIG. 1A illustrates change in CT26 tumor volume in Balb/cJ mice that receive rat IgG2a PD-1 antibody (control).
Figure 1B:
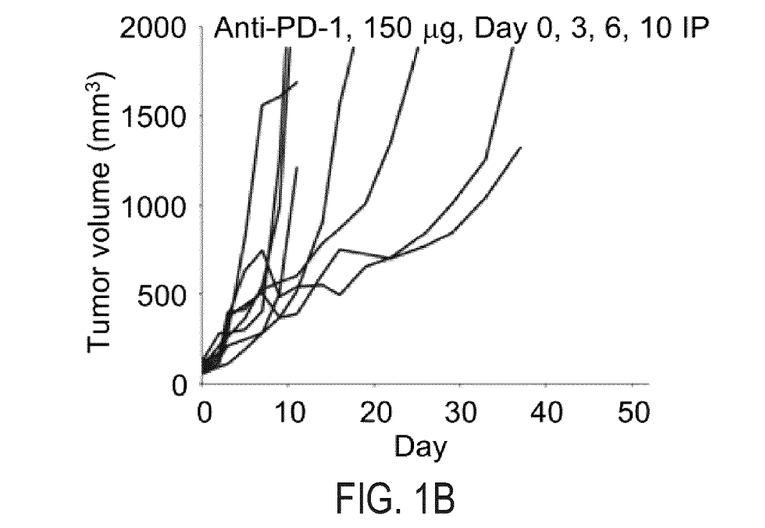
FIG. 1B illustrates change in CT26 tumor volume in Balb/cJ mice that receive 150 μg of rat IgG2a anti-PD-1 antibody on Days 0, 3, 6 and 10.
Figure 1C:
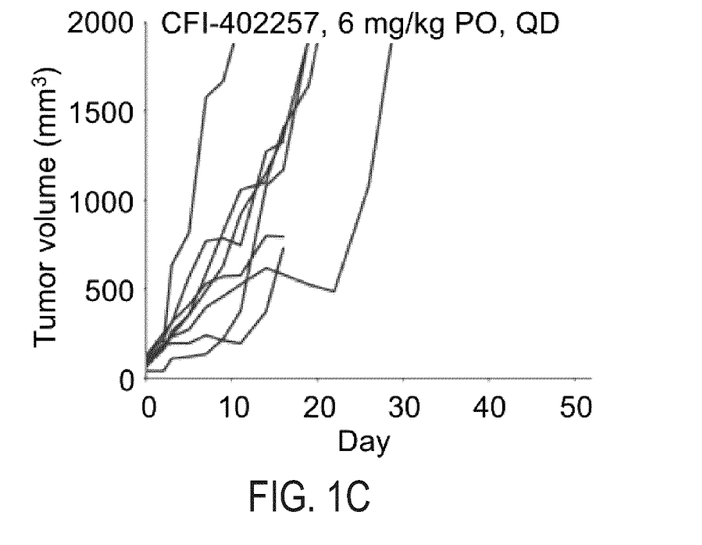
FIG. 1C illustrates change in CT26 tumor volume in Balb/cJ mice that receive 6 mg/kg of CFI-402257 daily for 21 days.
Figure 1D:
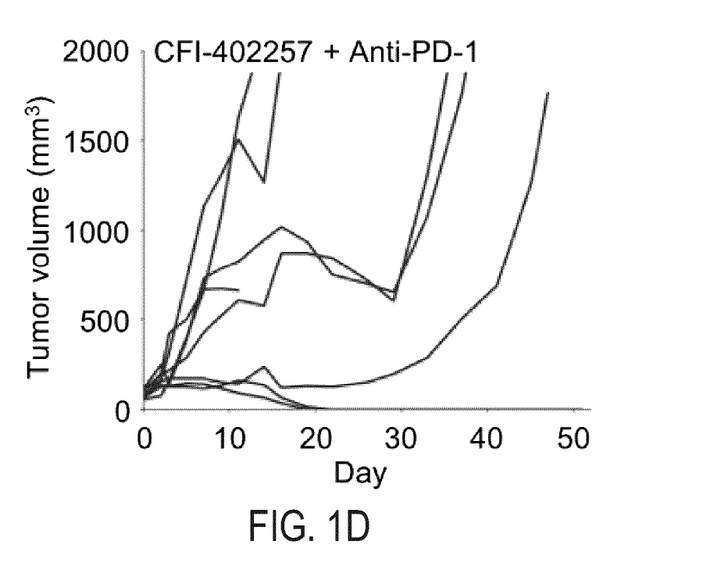
FIG. 1D illustrates change in CT26 tumor volume in Balb/cJ mice that receive the combination of 150 μg of rat IgG2a anti-PD-1 antibody on Days 0, 3, 6 and 10 and 6 mg/kg of CFI-402257 daily for 21 days.
Figure 2A:
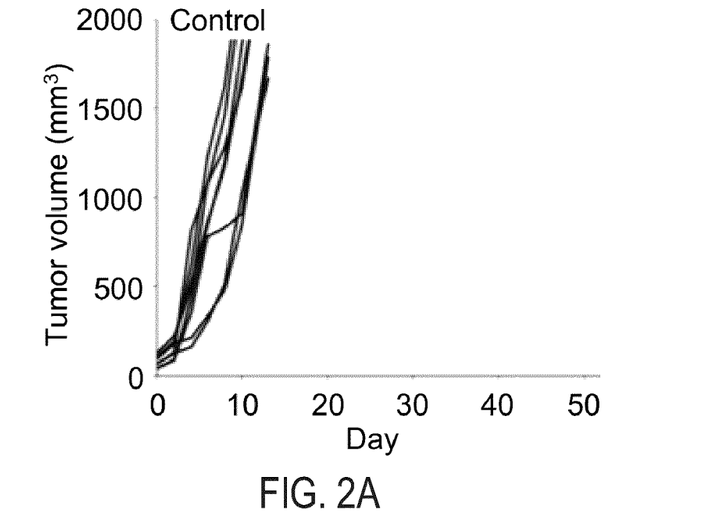
FIG. 2A illustrates change in CT26 tumor volume in Balb/cJ mice that receive rat IgG2a PD-1 antibody (control) in a duplicate experiment.
Figure 2B:
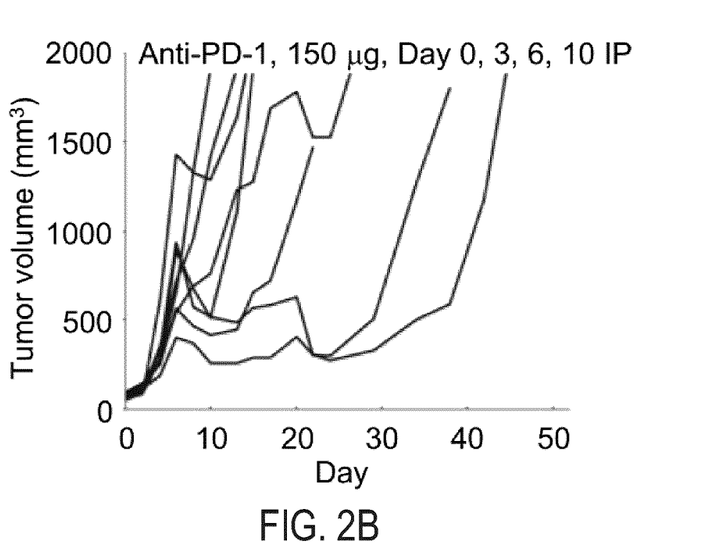
FIG. 2B illustrates change in CT26 tumor volume in Balb/cJ mice that receive 150 μg of rat IgG2a anti-PD-1 antibody on Days 0, 3, 6 and 10 in a duplicate experiment.
Figure 2C:
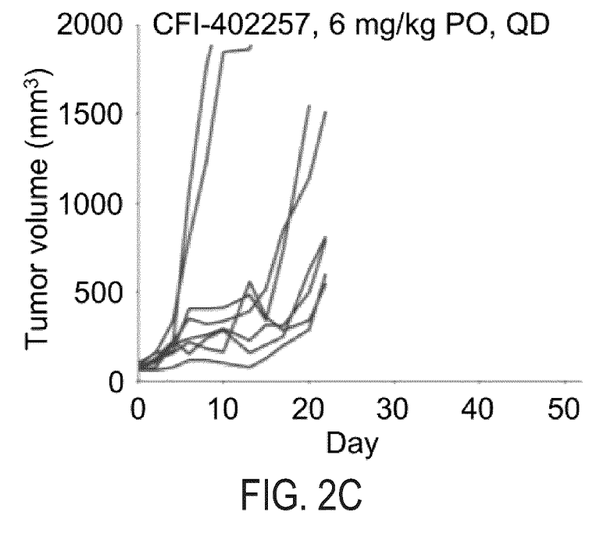
FIG. 2C illustrates change in CT26 tumor volume in Balb/cJ mice that receive 6 mg/kg of CFI-402257 daily for 21 days in a duplicate experiment.
Figure 2D:
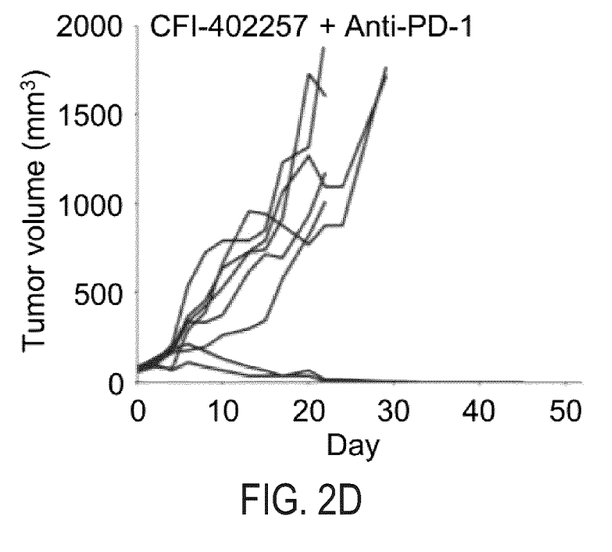
FIG. 2D illustrates change in CT26 tumor volume in Balb/cJ mice that receive the combination of 150 μg of rat IgG2a anti-PD-1 antibody on Days 0, 3, 6 and 10 and 6 mg/kg of CFI-402257 daily for 21 days in a duplicate experiment.

Complete Regression in Combination CFI-402257 and Anti-PD-1-Antibody-Treated Tumors The size of each individual tumor within each treatment arm is plotted (See FIGS. 1A-1D and 2A-2D). As can be seen in FIGS. 1A and 2A, tumors in the vehicle-treated control arm grew rapidly, and the average tumor was >1500 mm³ by Day 11 of treatment.

As shown in FIGS. 1B and 2B, there was tumor growth delay in the anti-PD-1-antibody-treated single agent arms. Similarly, the CFI-402257—treated single agent arm in FIGS. 1C and 2C indicate tumor growth delay and that the administered dosage was well-tolerated. Although there was tumor growth inhibition in both monotherapeutic arms, there were no instances in which complete regression was observed.

Surprisingly and notably, in the combination anti-PD-1 antibody and CFI-402257-treated arm of FIG. 1D, two of the eight tumors completely regressed. Very similar results were achieved in the duplicate experiment of FIG. 2D, where complete regression was again observed in two of eight tumors.

Example 4

CFI-402257 and Anti-PD-1-Antibody Generates Tumor Immunity

Furthermore, in the first experiment, the two animals in which complete regression had occurred were re-challenged by inoculation with CT26 cells on Day 31. Tumors did not grow in either mouse, indicating that immunity to the CT26 cells had been generated.

Example 5

Animal Body Weight Monitoring

In the first experiment, none of the animals receiving the CFI-402257 or anti-PD-1-antibody single agent treatment or the combination treatment recorded any significant body weight loss. Limited body weight loss (<7.5%) was observed only in animals treated with only CFI-402257 in the second experiment.

While the applicants have described a number of embodiments of this invention, it is apparent that these basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A method for treating colon cancer, comprising:
   administering to a subject an effective amount of a compound represented by the formula:

or a pharmaceutically acceptable salt thereof and an effective amount of a PD-1 inhibitor.

2. The method according to claim 1, wherein the PD-1 inhibitor is an antibody or an antigen binding fragment thereof.

3. The method according to claim 1, wherein the PD-1 inhibitor is a monoclonal antibody or an antigen binding fragment thereof.

4. The method according to claim 1, wherein the PD-1 inhibitor restores anti-tumor T-cell activity.

5. The method according to claim 1, wherein the PD-1 inhibitor blocks T-cell-inhibitory cell activity.

6. The method according to claim 1, wherein the PD-1 inhibitor is one selected from pembrolizumab and nivolumab.

7. The method according to claim 1, wherein the PD-1 inhibitor is one selected from JS001, SHR-1210, BGB-A317, IBI-308 and REGN2810.

8. A pharmaceutical composition comprising a compound represented by the formula:

or a pharmaceutically acceptable salt thereof and a PD-1 inhibitor.

9. The pharmaceutical composition according to claim 8, wherein the PD-1 inhibitor is an antibody or an antigen binding fragment thereof.

10. The pharmaceutical composition according to claim 8, wherein the PD-1 inhibitor restores anti-tumor T cell activity.

11. The pharmaceutical composition according to claim 8, wherein the PD-1 inhibitor blocks T-cell-inhibitory cell activity.

12. The pharmaceutical composition according to claim 8, wherein the PD-1 inhibitor is one selected from pembrolizumab and nivolumab.

13. The pharmaceutical composition according to claim 8, wherein the PD-1 inhibitor is one selected from JS001, SHR-1210, BGB-A317, IBI-308 and REGN2810.

\* \* \* \* \*

UNITED STATES PATENT AND TRADEMARK OFFICE
CERTIFICATE OF CORRECTION

PATENT NO. : 11,766,437 B2
APPLICATION NO. : 16/635320
DATED : September 26, 2023
INVENTOR(S) : Mark Robert Bray et al.

It is certified that error appears in the above-identified patent and that said Letters Patent is hereby corrected as shown below:

On the Title Page

Item (30) replace "August 1, 2018 (WO)" with --August 1, 2017 (CA)--.

Signed and Sealed this
Thirteenth Day of February, 2024

Katherine Kelly Vidal
*Director of the United States Patent and Trademark Office*